United States Patent
Alldredge

[11] Patent Number: 5,809,996
[45] Date of Patent: *Sep. 22, 1998

[54] COLLAPSIBLE METERED DOSE INHALER

[76] Inventor: Andrew L. Alldredge, 1186 Brandywyn La., Buffalo Grove, Ill. 60089

[ * ] Notice: The term of this patent shall not extend beyond the expiration date of Pat. No. 5,571,246.

[21] Appl. No.: 740,762

[22] Filed: Nov. 1, 1996

Related U.S. Application Data

[62] Division of Ser. No. 389,917, Feb. 16, 1995, Pat. No. 5,571,246.

[51] Int. Cl.[6] .................................................. A61M 11/04
[52] U.S. Cl. ................................ 128/200.23; 128/200.14
[58] Field of Search ........................ 128/200.14, 200.23, 128/203.15, 203.23, 203.24

[56] References Cited

U.S. PATENT DOCUMENTS

| | | | |
|---|---|---|---|
| 4,292,966 | 10/1981 | Mono et al. | 128/200.23 |
| 4,641,644 | 2/1987 | Andersson et al. | 128/200.23 |
| 4,852,561 | 8/1989 | Sperry | 128/200.23 |
| 4,926,852 | 5/1990 | Zoltan et al. | 128/200.23 |
| 5,320,094 | 6/1994 | Laube et al. | 128/200.23 |

FOREIGN PATENT DOCUMENTS

| | | | |
|---|---|---|---|
| 009667 | 4/1980 | European Pat. Off. | 128/200.23 |
| 2110543 | 6/1983 | United Kingdom | 128/200.14 |

*Primary Examiner*—Aaron J. Lewis
*Assistant Examiner*—William J. Deane, Jr.
*Attorney, Agent, or Firm*—Charles F. Lind

[57] ABSTRACT

The disclosed inhalation apparatus is suited for easily administering aerosol medication via a metered dose pressurized canister. The apparatus has a collapsible tubular body comprised of axially nested rigid pieces including end pieces with opposite connections respectively for directing spray from the canister axially through the tubular body cavity from one connection toward the other connection serving as the user's tubular mouthpiece. The tubular body can be axially shifted between an expanded operational position of maximum body cavity volume and maximum separation between the end pieces and a collapsed storage position of minimum separation where the rigid pieces are nested together. The end pieces have end plates of substantially equal size with peripheries suited to be gripped by the user, and a tubular flange projected off of one end plate that cooperates in proximity with structure of the other end plate in the collapsed position, providing a protective housing overlying the rigid pieces when collapsed.

4 Claims, 2 Drawing Sheets

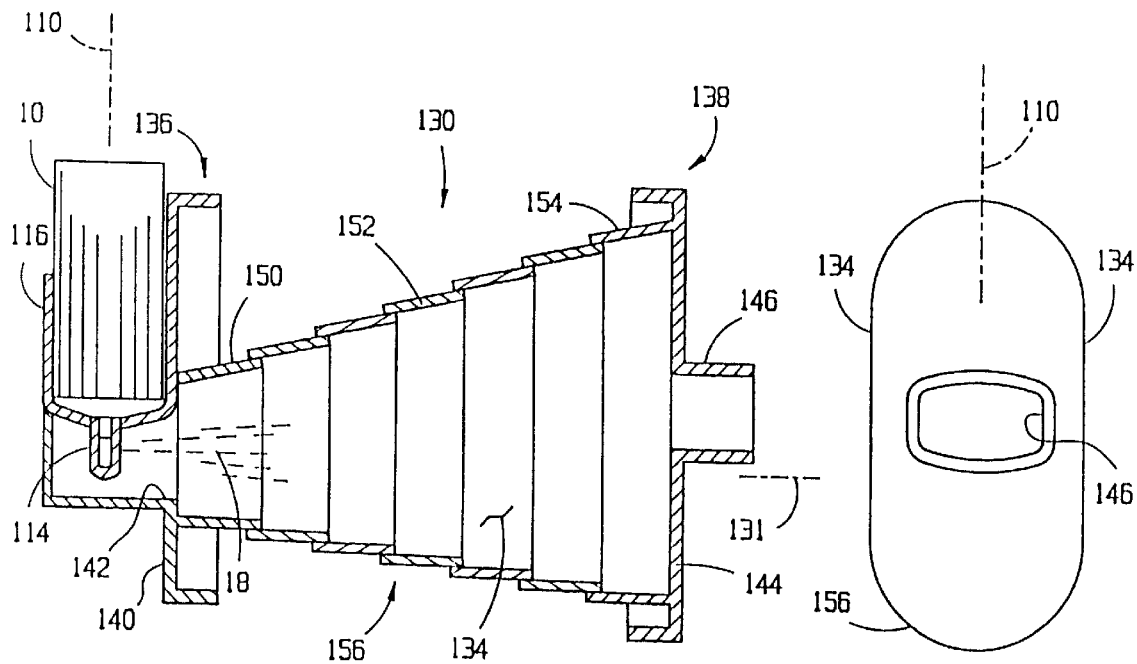
Fig. 7
Fig. 8
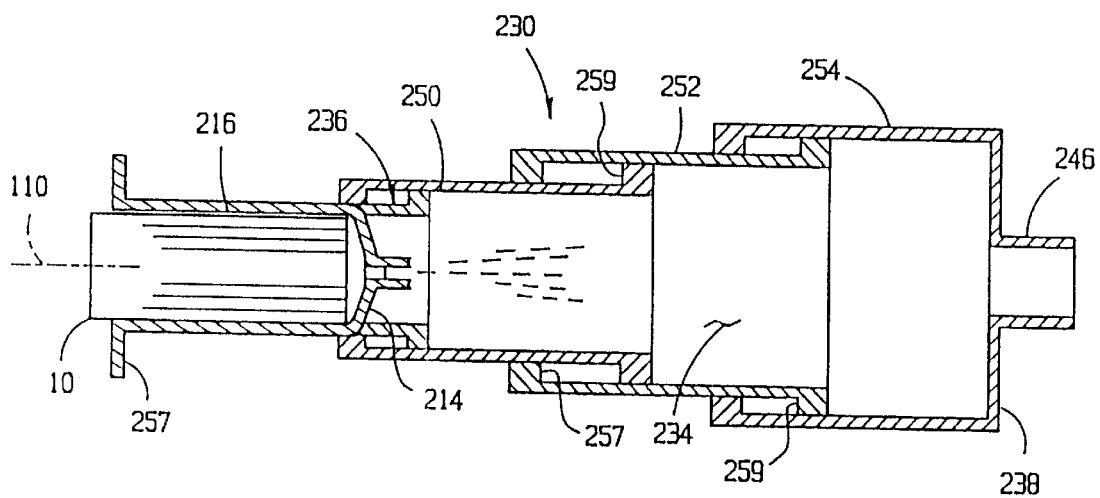
Fig. 9

COLLAPSIBLE METERED DOSE INHALER

RELATED APPLICATION

This is a Divisional application of application Ser. No. 08/389,917 filed Feb. 16, 1995, for COLLAPSIBLE METERED DOSE INHALER with the inventor identified as Andrew L. Alldredge, and issued on Nov. 5, 1996 as U.S. Pat. No. 5,571,246.

BACKGROUND OF THE INVENTION

Drugs of varying types, bronchodilators and steroids being two examples, have been available in pressurized aerosol canisters suited when manually actuated to deliver a small metered pulse of the drug, typically for administration into the opened mouth of the user. Simple dispensing devices are available to hold the canister, forming what is generally identified in the trade as an inhaler, thereby allowing the discharge as a misted spray to be accurately aimed into the user's open mouth. Many drugs however are intended to reach the user's lungs via the air passageways from the mouth, and misted sprays delivered from close range into the mouth largely tend to hit the inside mouth surfaces and become absorbed thereon, and thus never reach the lungs. The overall efficiency of any drug administered in this manner thus drops.

One form of inhaler has a tubular mouthpiece that can be held in the user's mouth, the interior of the mouthpiece defining a passageway somewhat concentrically around the spray discharge. This inhaler arrangement contains and more accurately directs the spray discharge into the mouth and further allows the user to breath deeply simultaneously when the spray enters the mouth. Clearance spaces provided in the inhaler allow for this breathing air flow via the inhaler to the mouth. Such inhalers help mix the combined inhaled air and misted drug, but yet are not very efficient as much of the sprays still strikes and remains on the user's mouth surfaces.

This is due to the close proximity of the actual exit point of the spray from the canister/inhaler and the user's mouth, whereby the high velocity misted but nonetheless large spray droplets of the discharged drug cannot navigate the nearby abrupt turns of the user's air passageways without striking and being absorbed thereon.

To overcome this drawback, some dispensing devices now provide a greater separation between the actual exit point of the spray from the canister/inhaler and the user's mouth, to allow the mist droplets to admix with and become more thoroughly atomized within the moving air. This greatly increases the percentage of the dispensed drug that reaches the user's lungs.

U.S. Pat. No. 4,470,412 illustrates a basic dispensing device inhaler with a tubular mouthpiece and structure for holding the drug canister, with the metered spray discharge being directed through the mouthpiece and into the user's mouth. The patent further illustrates an example of an extender device usable with this basis inhaler, comprised basically as a fixed tube having structures at its opposite ends suited to offer a separable connection to the inhaler mouthpiece and a different mouthpiece for the user's mouth. The hollow tube body increases the separation between the canister/inhaler spray exit point: and the user's mouth, while defining a constrained flow path for the spray droplets, allowing for longer common admixture time between the drug and moving air, for increased drug atomization and improved efficiency in drug administration to the user's lungs.

However, despite the possibility of improved drug administration, extender devices find limited use away from the medicine cabinet, except for the more critically suffering patients, as they are too large for convenient portable use.

U.S. Pat. No. 4,484,577 illustrates another dispensing device that has a fixed tubular extender with a mouthpiece at one end and a bellows at the opposite end, and with midpoint structure suited to hold a drug canister to discharge the drug into the bellows. When using the dispensing device, the user's mouth would be positioned over the mouthpiece and the bellows would be fully expanded, whereupon the user would inhale simultaneously with the drug being discharged into the bellows, to collapse the bellows and draw the combined bellows air/drug into the user's lungs via the mouth. While this device can increase the efficiency of drug delivery to the user's lungs, the device is difficult to use with the needed inhalation to collapse the bellows. Further, the collapsible bellows can be quite fragile, negating much of the appeal its compact size might offer for portable use.

SUMMARY OF THE INVENTION

This invention relates to metered dose inhalers, and particular those that are intended to administer the discharged drug more to the user's lungs than mouth for its effective use.

A basis object of this invention is to provide inhaler structure that is collapsible, to be compact in size in its collapsed condition, for adding to its appeal for universal and/or portable use, while yet offering improved and effective drug delivery to the user.

Another object of this invention is to provide collapsible inhaler structure that is easy to make and structurally durable in use, and that is easy to use.

Yet another object of this invention is to provide collapsible inhaler structure in the form of an accessory or add-on device for use with commercially available inhalers, for enhancing their overall drug administering efficiency, while yet being suited for portable use.

In an accessory mode, a collapsible tubular body structure defines a through cavity and connection means at the opposite ends thereof. The connection means at one end is suited for holding the tubular mouthpiece of conventional commercially available inhalers, to provide that the generally unidirectional output spray therefrom is axially directed through the cavity toward the second connection means at the other end. The second connection means includes another generally tubular mouthpiece, to be fitted into the user's mouth. The axially collapsible tubular body structure allows extended separation between the first and second connection means, whereby atomization of the output spray can be enhanced for effective drug delivery to the user's lungs; and allows a compact accessory when collapsed suited for portable storage and use when needed.

In an unitary inhaler mode, instead of the inhaler holding means being formed at the one end of the collapsible tubular body, the tubular body would have structure for holding the pressurized aerosol canister and for directing the generally unidirectional output spray therefrom axially through the defines cavity toward the mouthpiece at the other end.

The tubular body might be comprised as a plurality of generally annular pieces of different sizes, including adjacent telescoping pieces that virtually nest in a compact collapsed position and that only partly nest in an axially extended open position. The pieces can be annular segments of generally conical shapes to allow free axial movement between the opposite collapsed and expanded positions.

BRIEF DESCRIPTION OF THE DRAWINGS

These and other objects, features or advantages of the invention will be more fully understood and appreciated after consideration of the following description, which includes as a part thereof the accompanying drawings, wherein:

FIGS. 7 and 8 correspond to FIGS. 2 and 6, except illustrating an alternative embodiment of a collapsible inhaler;

FIG. 9 illustrates a center sectional view of yet a third embodiment of a collapsible inhaler, showing it in an intermediate position neither fully collapsed nor fully extended.

DETAILED DESCRIPTION OF PREFERRED EMBODIMENTS OF THE INVENTION

Figure 1:
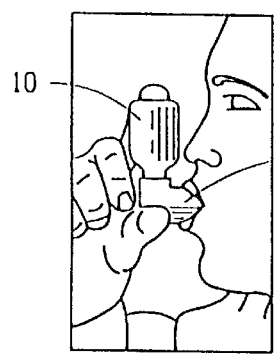
FIG. 1 is a side elevational view of a prior art aerosol drug canister and inhaler, positioned in the mouth of its user.
Figure 2:
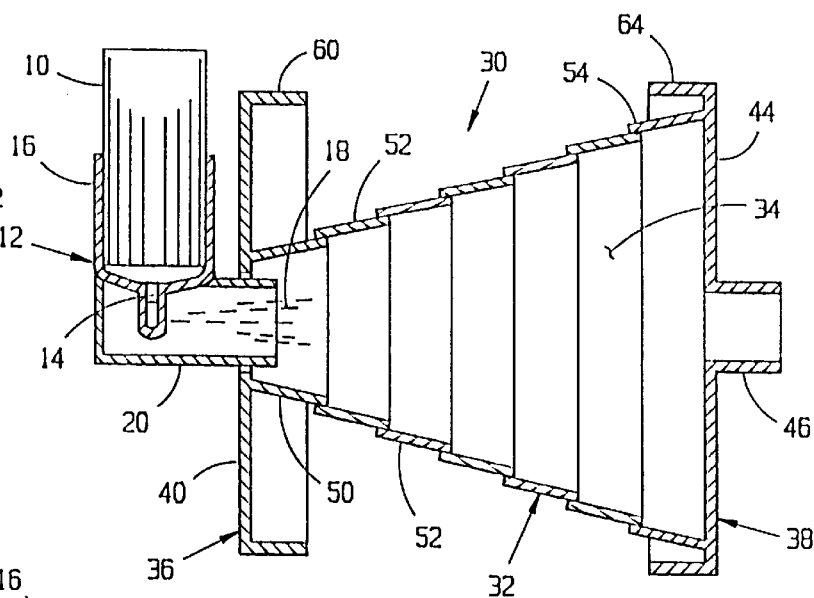
FIG. 2 is an enlarged center sectional view of the inhaler of FIG. 1, except being positioned in an inhaler extender of this invention, and not showing the user's mouth.
Figure 3:
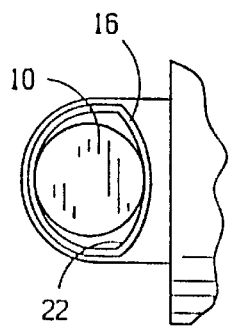
FIG. 3 is a top view of the drug canister, inhaler, and part of the inhaler extender of FIG. 2.
Figure 5:
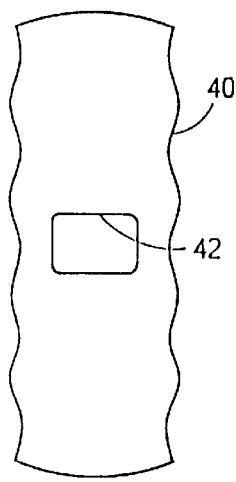
FIGS. 5 and 6 are opposite end elevational views of the inhaler extender of FIG. 4.
Figure 4:
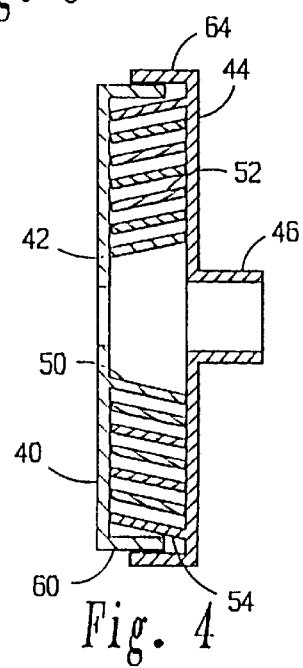
FIG. 4 is a view similar to FIG. 2, except illustrating the inhaler extender in its collapsed condition.
Figure 6:
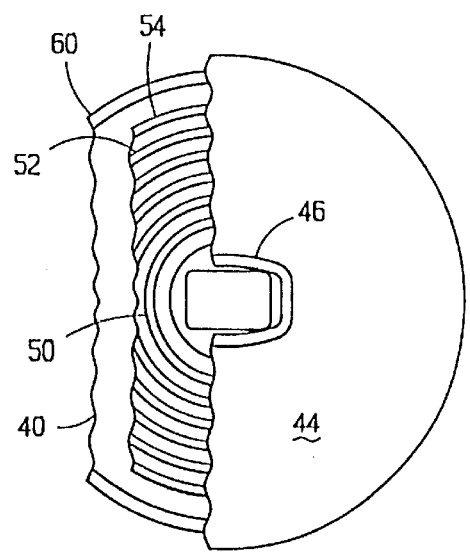

A basic prior art inhaler is illustrated in FIGS. 1, 2 and 3, comprised of an aerosol drug canister 10 fitted into a right angle inhaler device 12. The canister 10 contains under pressure the drug to be dispensed, and has a valve stem and outlet fitted into nozzle structure 14 of the inhaler device 12. The inhaler device wall 16 is sized and shaped to hold the canister 10 stably, while allowing it to be shifted relative to the inhaler device and into the nozzle structure 14, to release a meter pulse of the drug, typically as conical spray 18. The inhaler device 12 defines a generally tubular mouthpiece 20, and the nozzle structure 14 aims the pulsed spray 18 axially through the mouthpiece. The cooperating inhaler device-canister further provides clearance openings 22 for allowing air flow past the nozzle structure 14 and out the mouthpiece 20.

To use the inhaler, the mouthpiece 20 normally would be positioned in the user's mouth, whereupon the user then simultaneously inhales and activates the canister discharge, in an effort to suck into the lungs the discharged drug spray 18 and air flow via openings 22. However as noted above, this in not too effective, as much of the spray hits the user's mouth surfaces and is absorbed.

FIGS. 2–6 illustrate the invention as an accessory mode extender 30, comprised as a collapsible tubular body 32 defining a through cavity 34, and connection means 36 and 38 at the opposite body ends. The connection means 36 at one body end includes a plate 40 having an opening 42 suited for receiving and loosely holding the tubular mouthpiece 20 of the conventional prior art inhaler 12, to direct the output spray 18 axially through the cavity 34 toward the second connection means 38. The second connection means includes a plate 44 having a generally tubular mouthpiece 46 that is open to the cavity 34, but otherwise that is generally similar in shape to the mouthpiece 20 of the inhaler 12.

The tubular body 32 illustrated is comprised as a plurality of nested generally annular pieces of different sizes, including end pieces 50 and 54 connected to the respective adjacent plate 40 and 44, and adjacent intermediate pieces 52. The adjacent pieces telescope into or nest within one another in the collapsed condition of FIG. 4, but when axially separated bind across a smaller nested region of overlap as illustrated in FIG. 2, defining a fully extended condition whereat the end connection plates 40 and 44 are at maximum separation.

The inhaler extender would be used in the expanded position with the mouthpiece 46 being in the user's mouth, whereupon the user would then simultaneously inhale and activate the canister discharge. However, the discharged drug spray 18 would now have to travel the length of the generally containing cavity 34, admixing with the air therein and the air flow allowed via openings 22 and any clearance gaps around the inhaler mouthpiece 20 and plate opening 42 and between the adjacent annular pieces. This added length of commingled flow of the drug spray and available air before any of the drug is admitted into the user's mouth provides for vastly improved drug distribution to the user's lungs, since the lighter more completely atomized drug particles can more readily navigate the curved air passages between the user's mouth and lungs, without merely being absorbed on the mouth or any of these surfaces.

Commonly, the annular pieces can be made with approximately the same widths, or axial lengths. When the adjacent pieces are then completely nested in the collapsed condition of FIG. 4, the end plates are close together in a compact condition and are separated by approximately the maximum width of the widest of the annular pieces.

The end plates 40 and 44 are extended radially to annular in-turned flanges 60 and 64 respectively, that are sized to telescope together and enclose the exterior of the tubular body pieces, for durable storage in the collapsed position. Detent means (not shown) can be used to releasibly hold the flanges overlapped when the extender is closed. A cover (not shown) can be used also to fit over the mouthpiece during storage, for keeping it clean and sanitary.

The annular pieces 50, 52 and 54 can be formed as generally concentric conical segments, with the opening at the small end of each piece being slightly smaller than the opening of the large end of the adjacent nested piece. This allows free axial movement of the pieces between the fully extended bound position of FIG. 2 and the fully nested collapsed position of FIG. 4. The expanding conical cavity within the tubular body further would match the natural conical expansion of the discharged spray 18.

It can be observed that the illustrated tapers of the conical segments are quite large for clarity of disclosure, and would probably be much less in the fabrication of an actual extender, thereby providing even greater axial separation than illustrated without having the large end piece 54 that much larger than the small end piece 50. Moreover, the number of separate annular pieces can be varied, as can the widths or axial lengths thereof, to establish the desired length of the overall containing cavity 34.

The tapers of the adjacent nested annular pieces need not be complementary, but the larger piece can be tapered less than the smaller piece, to reduce flush surface contact over the annular overlapped binding region and to allow easy release of the bound pieces when closing the extender from its opened condition.

FIGS. 7 and 8 illustrate an inhaler extender 130 where the annular pieces 150, 152 and 154 could be made elliptical to have more flattened opposed sides 134, that would generally be lined up vertically, yielding more compactness for convenience of portability with only minor sacrifice of overall effectiveness. Specifically, the drug canister 10 normally will be extended vertically when in operation, and would fit in exhaler structure 130 to lie laterally of the axis of telescoping extension of the tubular body 130, with the longitudinal canister center axis 110 being normal to the telescoping direction 131. The tubular body 130 would be narrowed to provide that the flattened sides 134 might correspond more to and only slightly exceed the width (or diameter) of the canister 10.

Further, the taper of the telescoping bottom region 156 of the tubular body would be less than the taper of the telescoping top region of the tubular body, to have an asymmetrically shaped tubular body 130 (see FIG. 7). The inlet opening 142 in the smaller end plate 140 could also be vertically offset, being closer to the bottom, while the mouthpiece 146 could be centered vertically in the-larger end plate 144. This configuration provides even greater compactness, while yet sacrificing little in vastly improving the drug distributing effectiveness compared to the widespread use of the inhaler 12 without any extender Advantageously, this configuration could provide canister holding means 116 and nozzle structure 114 formed integrally of and at the small end connection means 136 near end plate 140 of the collapsible tubular body, for holding the aerosol drug canister 10 and for directing the drug spray 18 therefrom axially through the defined cavity 134 toward the mouthpiece 146 at the other generally larger end connection 138. Thus, no inhaler device 12 is needed to use this inhaler extender 130.

The tapers at the bottom regions 156 and at the sides near the bottoms of the nesting components could be made very small, approaching being cylindrical, and shoulders (not shown in FIG. 7) of conventional construction could be added to the adjacent nested pieces, operable to abut at the fully extended position.

FIG. 9 illustrates collapsible tubular body 230 comprised of generally cylindrical nested pieces 250, 252 and 254 that again is particularly suited for forming a unitary inhaler extender. In-turned shoulders 257 and out-turned shoulders 259 on the nested pieces engage to determine the opposite collapsed and extended positions (neither being shown). Canister holding meant 216 and nozzle structure 214 formed integrally of small end connection means 236 hold the aerosol drug canister 10 and direct the drug spray 18 therefrom axially through the defined cavity 234 toward the mouthpiece 246 at the other generally larger end connection 238. The canister 10 however would be aligned with its longitudinal-center axis 110 concentrically of the telescoping axis 231 of the tubular body 230.

Because the drug canister 10 is longer axially than its diameter and because the axial lengths of the end connection piece 236 and the telescoping annular pieces 250, 252 and 254 could be about the same length as the canister itself, and still nest completely, a similar maximum axial separation between the nozzle structure 214 and mouthpiece 246 will be provided with fewer separate pieces overall. Moreover, the overall lateral size of the collapsed extender body 230 need only slightly exceed the diameter of the drug canister.

It thus can be appreciated that each of the illustrated tubular bodies 30, 130 and 230 easily provides for significant axial expansion of the spray containing cavity between the collapsed or closed positions and the expanded or opened positions, allowing the spray discharge therein to admix and atomize with the common air flow for passage via the mouthpiece 46, 146 and 246 into the user's lungs. Moreover, the compact unit provides appeal for convenient portable storage and use.

The annular pieces forming each collapsible tubular body of the inhaler extender or inhaler 30, 130 or 230 are substantially rigid, and cooperate without any needed flexure or bending when being shifted between the collapsed storage and opened operational positions, for expected durability and trouble-free usage. The pieces can be formed of low cost but durable, materials, such as plastic, for reducing overall costs and allowing for widespread distribution and usage, even as a give-away marketing premium with the sale of the drug canister.

While specific embodiments have been illustrated, it will be obvious that minor changes could be made therefrom without departing from the spirit of the invention. Accordingly, the invention is to determined by the scope of the following claims.

What is claimed is:

1. For use with a metered dose pressurized canister having an outlet opened by a shiftable valve stem for discharging a pulsed output spray, a collapsible inhaler comprising a first annular end piece including an aperture for accepting the output spray of the canister;

a second annular end piece including a mouthpiece;

at least one annular body piece adequately sized and cooperatively arranged adjacent and between said first and second pieces, for effectively defining an axial through cavity between said aperture and said mouthpiece and for having said pieces telescoped and shifted respectively between an operative configuration of maximum separation between the end pieces and maximum cavity volume and a collapsed nested storage configuration of minimum separation between the end pieces;

the end pieces having end plates with peripheries thereon of closely related sizes, and said second end piece including a peripheral flange extended from its end plate in the direction axially of the telescoped shifting of the pieces and toward the first end piece, said end plate periphery and flange being suited to be gripped for shifting the tubular body pieces between the expanded operational and collapsed storage positions, and said flange being radially spaced from the telescoped portion of the second piece operable in the collapsed nested storage configuration to overlie said body piece and to present a convenient peripheral exterior for the collapsed inhaler.

2. A collapsible inhaler according to claim 1, further comprising the first end piece having structure unitary therewith for holding the canister and shiftable valve stem, for providing for said output spray into the cavity and for flow toward the other of the end pieces without the need of any other accessory device being used with the canister, the first end piece unitary structure being sized and oriented to hold the canister elongated coaxially in the direction of the telescoped shifting of the pieces and fitted within the telescoped portion of the first end piece, to shift with the first end piece and be telescoped within the adjacent body pieces and thereby provide a compact overall storage configuration for the held canister and inhaler that not much larger than the overall size of the nested inhaler storage configuration by itself.

3. A collapsible inhaler according to claim 1, further comprising the first end piece having structure unitary therewith for holding the canister and shiftable valve stem, for providing for said output spray into the cavity and for flow toward the other of the end pieces without the need of any other accessory device being used with the canister, the first end piece unitary structure including an end plate sized and oriented to hold the canister elongated in the direction and substantially normal to the telescoped shifting of the pieces and axially adjacent the telescoped portion of the first end piece, and said annular pieces being elliptically elongated and shortened in the same length and width directions as the elongated canister is held in the first end piece, and the flange being sized only slightly in exceed of the length and width dimensions of the canister for providing a compact overall storage configuration for the held canister and inhaler that not much larger than the overall size of the nested inhaler storage configuration by itself.

4. A collapsible inhaler according to claim 3, further comprising said aperture in the first end piece being asymmetrical between the shortened dimensions of the piece.

* * * * *